(12) United States Patent
Takato (10) Patent No.: US 10,649,201 B2
(45) Date of Patent: May 12, 2020

(54) OBJECTIVE OPTICAL SYSTEM

(71) Applicant: OLYMPUS CORPORATION, Hachioji-shi, Tokyo (JP)

(72) Inventor: Hideyasu Takato, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 106 days.

(21) Appl. No.: 16/025,745

(22) Filed: Jul. 2, 2018

(65) Prior Publication Data

US 2018/0314054 A1 Nov. 1, 2018

Related U.S. Application Data

(63) Continuation of application No. PCT/JP2016/083354, filed on Nov. 10, 2016.

(30) Foreign Application Priority Data

Jan. 6, 2016 (JP) .................................. 2016-001142

(51) Int. Cl.
*G02B 23/24* (2006.01)
*A61B 1/00* (2006.01)
(Continued)

(52) U.S. Cl.
CPC .............. *G02B 23/243* (2013.01); *A61B 1/00* (2013.01); *G02B 13/04* (2013.01); *G02B 23/26* (2013.01);
(Continued)

(58) Field of Classification Search
CPC ... A61B 1/05; A61B 1/00096; A61B 1/00163; A61B 1/00195; G02B 23/243;
(Continued)

(56) References Cited

U.S. PATENT DOCUMENTS 4,312,572 A 1/1982 Yamashita et al.
4,403,837 A * 9/1983 Nakahashi ............... G02B 9/60
359/740

(Continued)

FOREIGN PATENT DOCUMENTS

CN 104937470 A 9/2015
JP 61044283 B2 10/1986
(Continued)

OTHER PUBLICATIONS

International Preliminary Report on Patentability (IPRP) and English translation thereof dated Jul. 10, 2018, issued in International Application No. PCT/JP2016/083354.
(Continued)

*Primary Examiner* — Evelyn A Lester
(74) *Attorney, Agent, or Firm* — Holtz, Holtz & Volek PC

(57) ABSTRACT

The objective optical system consists of order from an object side, a first group having a positive refractive power, a second group having a negative refractive power, and a third group having a positive refractive power, wherein focusing is carried out by moving the second group, and a lens nearest to image is a planoconvex positive lens having a convex surface directed toward the object side, and a flat surface of the planoconvex positive lens is either affixed directly to an image pickup surface or cemented to a cover glass formed on the image pickup surface, and the objective optical system satisfies the following conditional expression (1).

$$5 < f\!f/f < 8 \qquad (1)$$

where,
ff denotes a focal length of the planoconvex positive lens disposed nearest to image, and
f denotes a focal length of the overall objective optical system at the time of normal observation.

2 Claims, 9 Drawing Sheets

(51) Int. Cl.
  *G02B 13/04* (2006.01)
  *G02B 23/26* (2006.01)
  *G02B 21/02* (2006.01)
  *G02B 13/18* (2006.01)
  *A61B 1/05* (2006.01)

(52) U.S. Cl.
  CPC ......... *A61B 1/0019* (2013.01); *A61B 1/00096* (2013.01); *A61B 1/00163* (2013.01); *A61B 1/00195* (2013.01); *A61B 1/05* (2013.01); *G02B 13/18* (2013.01); *G02B 21/02* (2013.01); *G02B 23/24* (2013.01); *G02B 23/2423* (2013.01)

(58) Field of Classification Search
  CPC ........ G02B 13/18; G02B 23/24; G02B 23/26; G02B 21/02; G02B 23/2423; G02B 13/04
  USPC ....... 359/656, 661, 716, 785, 786, 788, 798, 359/809, 810, 823; 600/101, 103, 109, 600/160, 162, 163, 167, 176
  See application file for complete search history.

(56) References Cited

U.S. PATENT DOCUMENTS

| | | | | |
|---|---|---|---|---|
| 4,764,001 A | * | 8/1988 | Yokota | G02B 13/04 359/740 |
| 4,867,546 A | * | 9/1989 | Nishioka | G02B 13/06 359/714 |
| 5,050,974 A | * | 9/1991 | Takasugi | A61B 1/04 359/663 |
| 6,433,937 B1 | | 8/2002 | Konno | |
| 9,341,838 B2 | | 5/2016 | Takato | |
| 2006/0268424 A1 | * | 11/2006 | Miyano | G02B 9/12 359/661 |
| 2009/0052062 A1 | * | 2/2009 | Fujiwara | G02B 21/02 359/784 |
| 2014/0155694 A1 | * | 6/2014 | Murata | G02B 23/243 600/109 |
| 2015/0359422 A1 | | 12/2015 | Igarashi | |

FOREIGN PATENT DOCUMENTS

| | | |
|---|---|---|
| JP | 04003851 B2 | 1/1992 |
| JP | 06317744 A | 11/1994 |
| JP | 11316339 A | 11/1999 |
| JP | 2000267002 A | 9/2000 |
| JP | 3765500 B2 | 4/2006 |
| JP | 2009163256 A | 7/2009 |
| WO | 2014208373 A1 | 12/2014 |

OTHER PUBLICATIONS

International Search Report (ISR) dated Jan. 24, 2017 issued in International Application No. PCT/JP2016/083354.
Written Opinion dated Jan. 24, 2017 issued in International Application No. PCT/JP2016/083354.
Chinese Office Action (and English language translation thereof) dated Jan. 20, 2020 issued Chinese Application No. 201680078238.3.

* cited by examiner

FIG. 7A
SA
FNO 3.003

FIG. 7E
SA
FNO 3.089

OBJECTIVE OPTICAL SYSTEM

CROSS-REFERENCE TO RELATED APPLICATION

The present application is a continuation application of PCT/JP2016/083354 filed on Nov. 10, 2016 which is based upon and claims the benefit of priority from Japanese Patent Application No. 2016-001142 filed on Jan. 6, 2016; the entire contents of which are incorporated herein by reference.

BACKGROUND OF THE INVENTION

Field of the Invention

The present invention relates to an objective optical system which has a focusing function, and particularly to an objective optical system for an endoscope which enables a close observation, and other objective optical systems which are suitable for photography by a small-size camera for household use.

Description of the Related Art

A commonly-used objective optical system for endoscope has a depth of field of a wide range of approximately 5 mm to 100 mm on an object side. An endoscope having such objective optical system installed thereon acquires an image by using mainly a CCD (charge coupled device) and CMOS (complementary metal-oxide semiconductor) as a solid image sensor.

In recent years, for improving an accuracy of diagnosis, a high image quality of endoscope images has been sought. Therefore, making the number of pixels large of an image sensor has been progressing. When an image sensor having a large number of pixels is used, for avoiding degradation of image quality due to diffraction, it is necessary to make small an F-number of an objective optical system. Moreover, in a case in which an image sensor having a large number of pixels is used, when the image sensor becomes large due to an effect of increase in the number of pixels, it is necessary to make large a focal length of the objective optical system as well.

For such reason, a depth of field of an objective optical system of endoscope using an image sensor having a large number of pixels has become narrow. Accordingly, for securing the depth of field of the same level as in the conventional technology, there has been an increasing need of an objective optical system which has a focusing function. Japanese Patent Publication after Examination No. Sho 61-044283, Japanese Patent Application Laid-open Publication No. Hei 06-317744, Japanese Patent Application Laid-open Publication No. Hei 11-316339 disclose objective optical systems for magnifying endoscope in which focusing to an object point at a short distance is possible. These objective optical systems include three lens groups having a positive refractive power, a negative refractive power, and a positive refractive power respectively. Japanese Patent Application Laid-open Publication No. 2000-267002 discloses an objective optical system for magnifying endoscope which includes three lens groups having a negative refractive power, a positive refractive power, and a negative refractive power respectively. Japanese Patent Application Laid-open Publication No. 2000-267002 discloses an objective optical system for endoscopes with a variable focal length, which includes two lens groups having a negative refractive power and a positive refractive power respectively. Japanese Patent Publication after Examination No. Hei 04-3851 discloses an objective optical system for endoscope having at least three lens groups having a negative refractive power, a positive refractive power, and a positive refractive power respectively, and in which focusing is possible.

Japanese Patent Application Laid-open Publication No. 2000-267002, Japanese Patent No. 3765500 Publication and Japanese Patent Publication after Examination No. Hei 04-3851 disclose the objective optical systems in which a field lens having a refractive power is disposed nearest to image-surface side of the objective optical system.

SUMMARY OF THE INVENTION

An objective optical system according to at least some embodiments of the present invention consists of in order from an object side, a first group having a positive refractive power, a second group having a negative refractive power, and a third group having a positive refractive power, wherein focusing is carried out by moving the second group, and a lens nearest to image is a planoconvex positive lens having a convex surface directed toward the object side, and a flat surface of the planoconvex positive lens is either affixed directly to an image pickup surface or cemented to a cover glass formed on the image pickup surface, and the objective optical system satisfies the following conditional expression (1).

$$5 < ff/f < 8 \qquad (1)$$

where, ff denotes a focal length of the planoconvex positive lens disposed nearest to image, and f denotes a focal length of the overall objective optical system at the time of normal observation.

DETAILED DESCRIPTION OF THE INVENTION

An objective optical system according to an embodiment will be described below by referring to the accompanying diagrams. However, the present invention is not restricted to the embodiment described below.

Figure 1A:
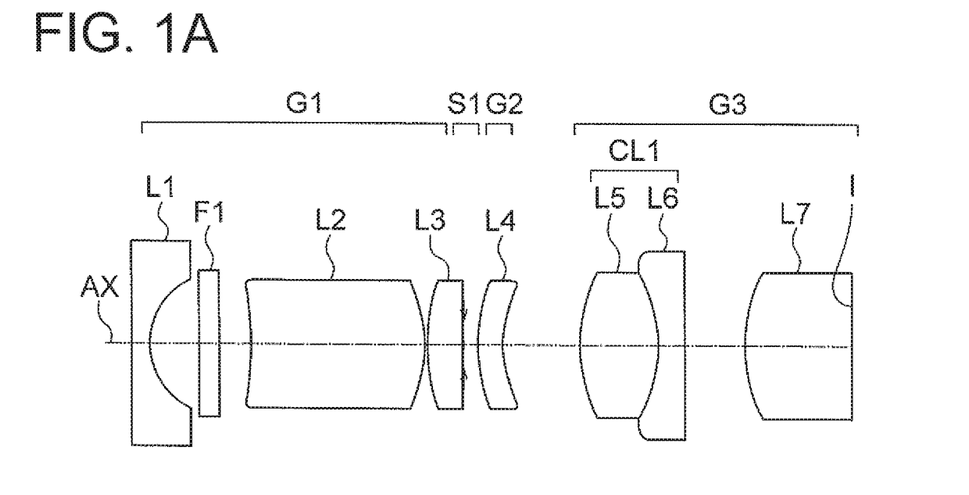
FIG. 1A, FIG. 1B, FIG. 1C, and FIG. 1D are lens cross-sectional views of an objective optical system according to an embodiment and less cross-sectional views near an image pickup surface.
Figure 1B:
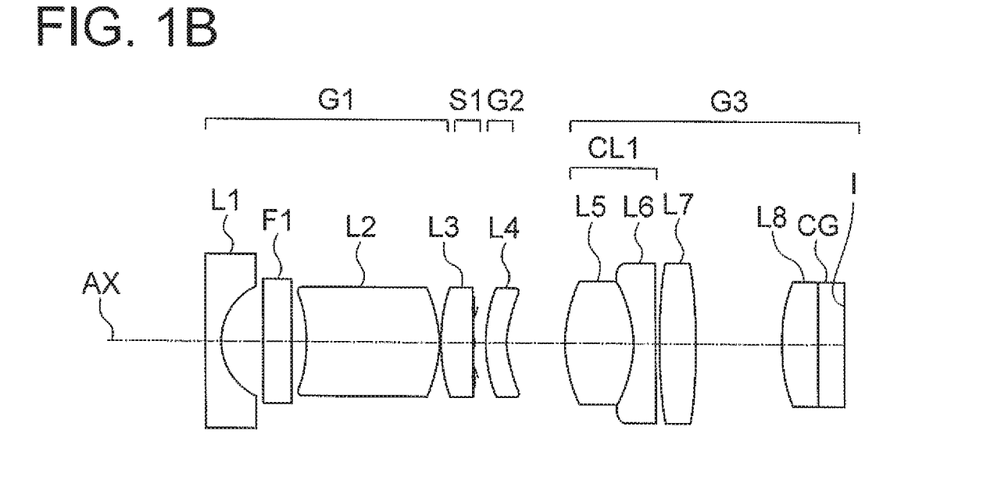

Lens cross-sectional views of each embodiment will be described below. FIG. 1A and FIG. 1B are lens cross-sectional views of the objective optical system according to the embodiment.

Lens cross-sectional views of each example will be described below. In FIG. 2A, FIG. 2B, FIG. 4A, FIG. 4B, FIG. 6A, FIG. 6B, FIG. 8A, and FIG. 8B, FIG. 2A, FIG. 4A, FIG. 6A, and FIG. 8A are lens cross-sectional views in a normal observation state of an objective optical system, and FIG. 2B, FIG. 4B, FIG. 6B, and FIG. 8B are lens cross-sectional views in a close observation state of an objective optical system.

Aberration diagrams of each example will be described below. In FIG. 3A, FIG. 5A, FIG. 7A, and FIG. 9A show a spherical aberration (SA) in the normal observation state, FIG. 3B, FIG. 5B, FIG. 7B, and FIG. 9B show an astigmatism (AS) in the normal observation state, FIG. 3C, FIG. 5C, FIG. 7C, and FIG. 9C show a distortion (DT) in the normal observation state, and FIG. 3D, FIG. 5D, FIG. 7D, and FIG. 9D shows a chromatic aberration of magnification (CC) in the normal observation state.

Moreover, FIG. 3E, FIG. 5E, FIG. 7E, and FIG. 9E show a spherical aberration (SA) in the close observation state, FIG. 3F, FIG. 5F, FIG. 7F, and FIG. 9F show an astigmatism (AS) in the close observation state, FIG. 3G, FIG. 5G, FIG. 7G, and FIG. 9G show a distortion (DT) in the close observation state, and FIG. 3H, FIG. 5H, FIG. 7H, and FIG. 9H show a chromatic aberration of magnification (CC) in the close observation state.

An objective optical system of a first embodiment includes in order from an object side, a first group G1 having a positive refractive power, an aperture stop S1, a second group G2 having a negative refractive power, and a third group G3 having a positive refractive power.

More specifically, as shown in FIG. 1A, the first group G1 having a positive refractive power includes in order from the object side, a first negative lens L1 having a concave surface directed toward an image side, a plane parallel plate F1, a second positive lens L2, and a third positive lens L3. The second group G2 includes a fourth negative lens L4. Focusing is carried out by moving the second group G2 along an optical axis AX. The third group G3 having a positive refractive power includes in order from the object side a fifth positive lens L5, a sixth negative lens L6, and a seventh positive lens L7. The fifth positive lens L5 and the sixth negative lens L6 are cemented and form a cemented lens CL1.

A lens nearest to image is the seventh positive lens L7 which is a planoconvex lens having a convex surface directed toward the object side. A flat surface of the seventh positive lens L7 which is a planoconvex lens is affixed directly to an image pickup surface I.

The aperture stop S1 is disposed between the first group G1 and the second group G2. Moreover, the plane parallel plate F1 is disposed between the first negative lens L1 and the second positive lens L2. It is possible to dispose the plane parallel plate F1 at an arbitrary position in the objective optical system.

FIG. 1B is a diagram showing a cross-sectional view of an arrangement of an objective optical system according to a second embodiment of the present invention. The objective optical system of the present embodiment includes in order from an object side, a first group G1 having a positive refractive power, an aperture stop S1, a second group G2 having a negative refractive power, and a third group G3 having a positive refractive power.

More specifically, as shown in FIG. 1B, the first group G1 having a positive refractive power includes in order from the object side, a first negative lens L1, a plane parallel plate F1, a second positive lens L2, and a third positive lens L3. The second group G2 includes a fourth negative lens L4. Focusing is carried out by moving the second group G2 along an optical axis AX. The third group G3 having a positive refractive power includes in order from the object side, a fifth positive lens L5, a sixth negative lens L6, a seventh positive lens L7, an eighth positive lens L8, and a cover glass CG.

The fifth positive lens L5 and the sixth negative lens L6 are cemented and form a cemented lens CL1. The eighth positive lens L8 and the cover glass CG are cemented.

A lens nearest to image is the eighth positive lens L8 which is a planoconvex lens having a convex surface directed toward the object side. A flat surface of the eighth positive lens L8 is cemented to the cover glass CG formed on an image pickup surface I.

The aperture stop S1 is disposed between the first group G1 and the second group G2. Moreover, the plane parallel plate F1 is disposed between the first negative lens L1 and the second positive lens L2. It is possible to dispose the plane parallel plate F1 at an arbitrary position in the objective optical system.

Figure 1C:
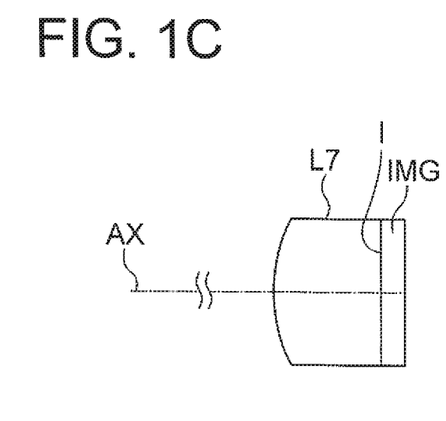
Figure 1D:
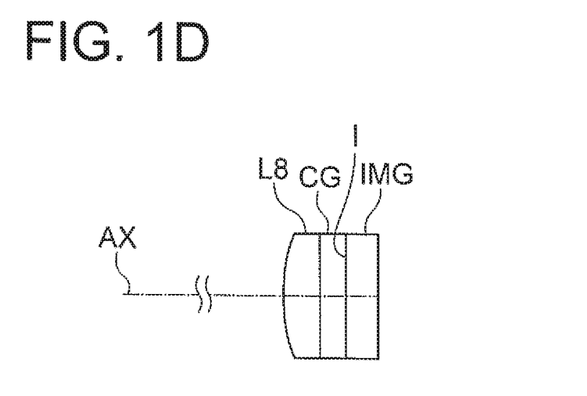

Moreover, as shown in FIG. 1C and FIG. 1D, in each embodiment, an image sensor IMG is disposed near the image pickup surface I of the objective optical system. In such manner, an image pickup optical system may be formed by assembling the objective optical system and the image sensor IMG.

Moreover, in each embodiment, it is desirable to satisfy the following conditional expression (1)

$$5 < ff/f < 8 \quad (1)$$

where, ff denotes a focal length of the planoconvex positive lens disposed nearest to image, and f denotes a focal length of the overall objective optical system at the time of normal observation.

Conditional expression (1) regulates a condition for letting the optical system to be optimum with regard to position adjustment of an image plane of the objective optical system.

Generally, at the time of adjusting a position of an image plane of an objective optical system, the overall objective optical system is to be moved along an optical axis AX. Accordingly, the optimum position of the image plane and the optimum position of an image pickup surface are adjusted. Here, in an objective optical system suitable for a high-definition small-size image sensor, a diameter of a circle of least confusion is extremely small. Consequently, error sensitivity becomes high for a position of the objective optical system.

Therefore, a lens having a positive refractive power is disposed on the image pickup surface side. Moreover, lenses to be moved at the time of adjusting the position of the image plane are let to be some of the lenses in the objective optical system. Accordingly, it is possible to weaken the refractive power of lenses to be moves at the time of adjusting the position of the image plane. As a result, it is possible to let it to be an objective optical system that is strong against the error sensitivity.

When a value falls below a lower limit value of conditional expression (1), since the focal length of the lens nearest to image becomes excessively small, it is possible to lower the error sensitivity. However, when the value falls below a lower limit value of conditional expression (1), a spherical aberration that occurs at the lens nearest to image becomes large. Consequently, the objective optical system may not be suitable for a high-definition image sensor.

When an upper limit value of conditional expression (1) is exceeded, an effect of reducing the sensitivity becomes small, and since imparting an optical refractive power to the lens disposed on the image pickup surface becomes almost meaningless, it is not preferable.

It is preferable to satisfy the following conditional expression (1') instead of conditional expression (1).

$$5.5 < ff/f < 6 \quad (1')$$

By satisfying conditional expression (1'), the effect of conditional expression (1) becomes even larger, and it is possible to lower the manufacturing-error sensitivity.

Moreover, an objective optical system which satisfies conditional expression (1'), regardless of the refractive power of each group, includes in order from an object side, three lens groups which are, a first group, a second group, and a third group. Moreover, focusing is carried out by moving only the second group along an optical axis. A lens disposed nearest to image is a planoconvex positive lens having a convex surface directed toward the object side. The planoconvex positive lens is either affixed directly to an image pickup surface or cemented to a cover glass formed on the image pickup surface.

By satisfying conditional expression (1') regardless of an arrangement of the refractive power of each lens group, it is possible to realize an objective optical system which is strong against the manufacturing-error sensitivity and in which the adjustment of the optimum position of the image plane is easy.

As shown in FIG. 1A, the seventh positive lens L7 disposed nearest to image is a planoconvex lens having a convex surface directed toward the object side. A flat surface on the image side of the seventh positive lens L7 is affixed directly to the image pickup surface I.

Moreover, as shown in FIG. 1B, the eighth positive lens L8 disposed nearest to image is a planoconvex lens having a convex surface directed toward the object side. A plane parallel plate for protecting the image pickup surface I is affixed to the image pickup surface I as the cover glass CG. A flat surface on the image side of the eighth positive lens L8 is affixed directly to the cover glass CG.

In such manner, it is desirable that the rearmost positive lens disposed nearest to image is affixed to the image pickup surface I, and in this case, the positive lens may be either affixed to the cover glass (plane parallel plate) CG or may be affixed directly on the image pickup surface I.

When the positive lens disposed nearest to image is not affixed to the image sensor, it is necessary to hold the lens leaving an air space from the image sensor. Consequently, not only that a holding member is newly required but also a frame member holding the image sensor makes a size large in an optical axial direction, and therefore it is not preferable.

Moreover, in the first embodiment and the second embodiment, the second group G2 includes the fourth negative lens L4. The fourth negative lens L4 is a negative meniscus lens having a convex surface directed toward the object side.

At the time of carrying out focusing with a fluctuation in a position of an object point from a time of normal observation to a time of close observation, it is necessary to carry out focusing by moving at least one group. The lens group that is to be moved for focusing may be any lens group out of the plurality of lens groups in the objective optical system.

Moreover, the lens group to be moved may be one or may be in plurality. When there is only one lens group that is movable, an effect that it is possible to simplify a mechanical structure of the objective optical system is shown.

As described above, in the objective optical systems of the first embodiment and the second embodiment, focusing is carried out by moving the second group G2. At the time of focusing, the fourth negative lens L4 moves along the optical axis AX.

For focusing, a method of moving the overall objective optical system or moving the image sensor may be taken into consideration. However, in this method, a weight of the lens group or the image sensor to be moved becomes heavy. Consequently, a load on a drive mechanism becomes heavy, or since it is necessary to make the mechanism large-sized, it is not preferable.

Moreover, it is desirable that the objective optical system according to the present embodiment satisfies the following conditional expression (2).

$$-24 < fg2/f < -8 \quad (2)$$

where,
fg2 denotes a focal length of the second group, and
f denotes the focal length of the overall objective optical system at the time of normal observation.

By satisfying conditional expression (2), it is possible to lower the error sensitivity at the time of focusing, and to suppress an aberration fluctuation.

When a value falls below a lower limit value of conditional expression (2), since the refractive power of the second group G2 becomes strong, the error sensitivity of the second group G2 on the image plane becomes high. Consequently, since shift in a focusing position on the image pickup surface becomes large due to shift in a position of the second group G2, it is not preferable.

When the value falls below the lower limit value of conditional expression (2), a degradation of optical performance due to tilting and decentering of the second group G2 at the time of focusing becomes remarkable.

When an upper limit value of conditional expression (2) is exceeded, a fluctuation in a curvature of field due to focusing becomes large, and since there is a significant difference in an image-plane position at the time of normal observation and at the time of close observation, it is not preferable.

Furthermore, for lowering the error sensitivity of the second group G2 at the time of focusing, it is preferable to satisfy the following conditional expression (2') instead of conditional expression (2).

$$-24 < fg2/f < -14 \quad (2')$$

By making an arrangement such that a value does not fall below a lower limit value of conditional expression (2'), it is possible to further reduce the degradation of optical performance due to decentering of the second group G2.

Moreover, it is desirable that the objective optical system according to the present embodiment satisfies the following conditional expression (3).

$$2 < rf/f < 4 \quad (3)$$

where,
rf denotes a radius of curvature of an object-side surface of the positive lens disposed nearest to image, and f denotes the focal length of the overall objective optical system at the time of normal observation.

Conditional expression (3) regulates a condition for restricting an angle of incidence on the image pickup surface. Since the image sensor is small-sized, an angle of incidence of light rays incident on the image sensor is required to be within a certain range.

When a value falls below a lower limit value of conditional expression (3), bending of light rays at the rearmost surface (image-side surface) of the rearmost lens disposed nearest to image becomes large, and the optical system becomes a telecentric optical system. However, since an light ray height becomes high, a diameter of the lens becomes large which is not preferable. Moreover, an amount of the spherical aberration that occurs at a surface of incidence of the rearmost lens also becomes large.

When an upper limit value of conditional expression (3) is exceeded, an angle of oblique incidence of a light ray on the image pickup surface becomes large. Consequently, a loss of quantity of light on each pixel becomes large, thereby causing reduction of light in a peripheral area, which is not preferable. Furthermore, when the upper limit value of conditional expression (3) is exceeded, since the refractive power of the lens nearest to image becomes weak, the range of conditional expression (1) is surpassed. Consequently, a problem such as, the effect of lowering the sensitivity at the time of adjusting the image-plane position of the objective optical system becoming small, arises.

Moreover, it is desirable that the objective optical system according to the present embodiment satisfies the following conditional expression (4).

$$0.15 < df/ff < 0.4 \tag{4}$$

where, df denotes a distance from an object-side surface of the positive lens disposed nearest to image up to the image pickup surface, and ff denotes a focal length of the positive lens disposed nearest to image.

When a value falls below a lower limit value of conditional expression (4), magnification of the rearmost positive lens disposed nearest to image becomes small. Consequently, the error sensitivity at the time of adjusting the image-plane position is not lowered. Even when a radius of curvature of the rearmost positive lens is set to be within a range of conditional expression (3), the effect becomes small.

When an upper limit value of conditional expression (4) is exceeded, the error sensitivity at the time of adjusting the image-plane position becomes excessively small, and an adjustment of large amount is to be made. Consequently, it is necessary to make long a length of a fitting portion of a lens barrel holding the image pickup surface and the rearmost positive lens and a lens barrel holding a lens before the rearmost positive lens, thereby making the overall lens barrel large, which is not preferable.

It is preferable to satisfy the following conditional expression (4') instead of conditional expression (4).

$$0.28 < df/ff < 0.4 \tag{4'}$$

By making an arrangement such that a value does not fall below a lower limit value of conditional expression (4'), an effect of making the error sensitivity of the image-plane position low becomes even larger.

Moreover, it is desirable that the objective optical system according to the present embodiment satisfies the following conditional expression (5).

$$0.2 < dn/f < 1.2 \tag{5}$$

where, dn denotes an amount of movement of the second group G2, and f denotes the focal length of the overall objective optical system at the time of normal observation.

When a value falls below a lower limit value of conditional expression (5), the amount of movement of the second group G2 at the time of focusing becomes excessively large, thereby contributing to making the overall length long and therefore is not preferable.

When an upper limit value of conditional expression (5) is exceeded, the error sensitivity of the second group G2 on the image plane becomes high. Particularly, in a wide angle optical system, when the error sensitivity is high, visual field vignetting is susceptible to occur, thereby causing a remarkable degradation of image quality. Furthermore, since a coma aberration due to decentering becomes large, a degradation of image in a peripheral portion of image field corresponding to a direction of decentering occurs, and therefore it is not preferable.

It is preferable to satisfy the following conditional expression (5') instead of conditional expression (5).

$$0.68 < dn/f < 1.2 \tag{5'}$$

By satisfying conditional expression (5'), the effect of conditional expression (5) becomes further large, and the effect of lowering the manufacturing-error sensitivity of the second group G2 becomes large.

Moreover, it is desirable that the objective optical system according to the present embodiment satisfies the following conditional expression (6).

$$-8 < fg2/fg1 < -4 \tag{6}$$

where, fg2 denotes the focal length of the second group G2, and fg1 denotes a focal length of the first group G1.

Conditional expression (6) regulates a condition for suppressing the image-plane fluctuation at the time of focusing by making appropriate the refractive power of the second group G2, and for contributing to small-sizing.

When a value falls below a lower limit value of conditional expression (6), since the refractive power of the second group G2 becomes weak, the amount of movement of the second group G2 becomes excessively large, thereby making the size of the overall system large.

When an upper limit value of conditional expression (6) is exceeded, a fluctuation in the curvature of field with the focusing becomes large, and there is a significant difference in the image-plane position at the time of normal observation and the image-plane position at the time of close observation, and therefore it is not preferable.

Moreover, it is desirable that the objective optical system of the present embodiment satisfies the following conditional expression (7).

$$-7.6 < fg2/fg3 < -2.4 \tag{7}$$

where, fg2 denotes the focal length of the second group G2, and fg3 denotes a focal length of the third group G3.

Conditional expression (7) regulates a condition for correcting the curvature of field appropriately.

When a value falls below a lower limit value of conditional expression (7), the image plane is inclined to over, and when an upper limit value of conditional expression (7) is exceeded, the image plane is inclined to under. Accordingly, an image is not focused at a central portion of image field and at a peripheral portion of image field, and therefore it is not preferable.

Moreover, it is desirable that the objective optical system according to the present embodiment satisfies the following conditional expression (8).

$$1.05 < r2/f < 1.45 \tag{8}$$

where, r2 denotes a radius of curvature of an image-side surface of the first lens L1 disposed nearest to object, and f denotes the focal length of the overall objective optical system at the time of normal observation.

Conditional expression (8) regulates a condition related to correction of an astigmatism and correction of a distortion. An endoscope image is basically to help secure a field of view by making the distortion large.

However, when a value falls below a lower limit value of conditional expression (8), since the distortion becomes excessively large, an angle of view becomes excessively large beyond necessity. As a result, an image is crushed in a peripheral portion, and it is not preferable. Furthermore, Petzval image plane is inclined largely to plus and the curvature of field becomes large.

When an upper limit value of conditional expression (8) is exceeded, a meridional image plane is inclined largely to under as well as the astigmatism becomes large, which is not preferable.

Moreover, it is desirable that the objective optical system according to the present embodiment satisfies the following conditional expression (9).

$$-0.34 < f1/ff < -0.18 \tag{9}$$

where, f1 denotes a focal length of the first lens L1 disposed nearest to object, and ff denotes the focal length of the positive lens disposed nearest to image.

Conditional expression (9) regulates a condition for lowering the error sensitivity related to the angle of view. An error in an air space between the first lens L1 and the second lens L2 contributes largely to a fluctuation of an angle of field. By letting the focal length of the first lens L1 to be in a range of conditional expression (9), an objective optical system which is strong against a manufacturing error is achieved.

When a value falls below a lower limit value of conditional expression (9), the refractive power of the first lens L1 becomes weak, and the manufacturing-error sensitivity becomes low. However, when an attempt is made to adjust the angle of field to be of an appropriate value by varying the air space between the first lens L1 and the second lens L2, an amount of adjustment becomes excessively large, thereby contributing to making the overall length long, and therefore it is not preferable.

When an upper limit value of conditional expression (9) is exceeded, the refractive power of the first lens L1 becomes excessively strong, and the manufacturing error with respect to the angle of field is susceptible to occur. Or, when the angle of field is adjusted, since an effect of fluctuation due to an error after the adjustment becomes large, it is not preferable.

Moreover, it is desirable that the objective optical system according to the present embodiment satisfies the following conditional expression (10).

$$1.2 < df/dn < 5.6 \tag{10}$$

where, df denotes the distance from the object-side surface of the positive lens disposed nearest to image up to the image pickup surface, and dn denotes the amount of movement of the second group G2.

Conditional expression (10) regulates a condition for lowering the manufacturing-error sensitivity of the image-plane position of the objective optical system.

When a value falls below a lower limit value of conditional expression (10), sensitivity of the image-plane position of the overall objective optical system with respect to the manufacturing error becomes high and it becomes difficult to maintain a constant balance of a near point and a far point of the observation depth.

When an upper limit value of conditional expression (10) is exceeded, the sensitivity of the image-plane position by position accuracy of the second group G2 which is movable becomes high. Consequently, a defect of shift in the focusing position corresponding to a shift in the position of the second group G2 due to manufacturing error is susceptible to occur, and therefore it is not preferable.

Example 1

Figure 2A:
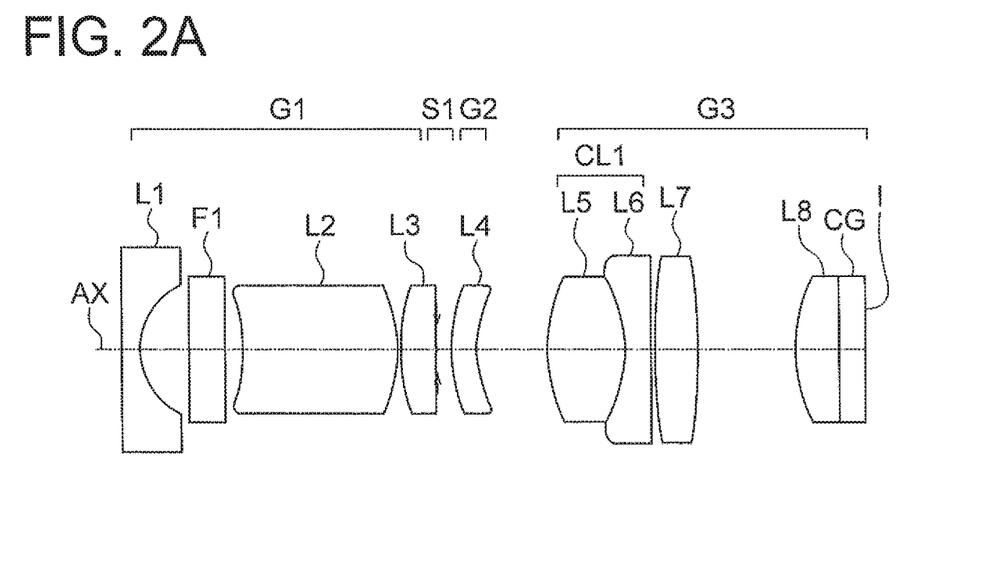
FIG. 2A and FIG. 2B are lens cross-sectional views of an objective optical system according to an example 1.
Figure 2B:
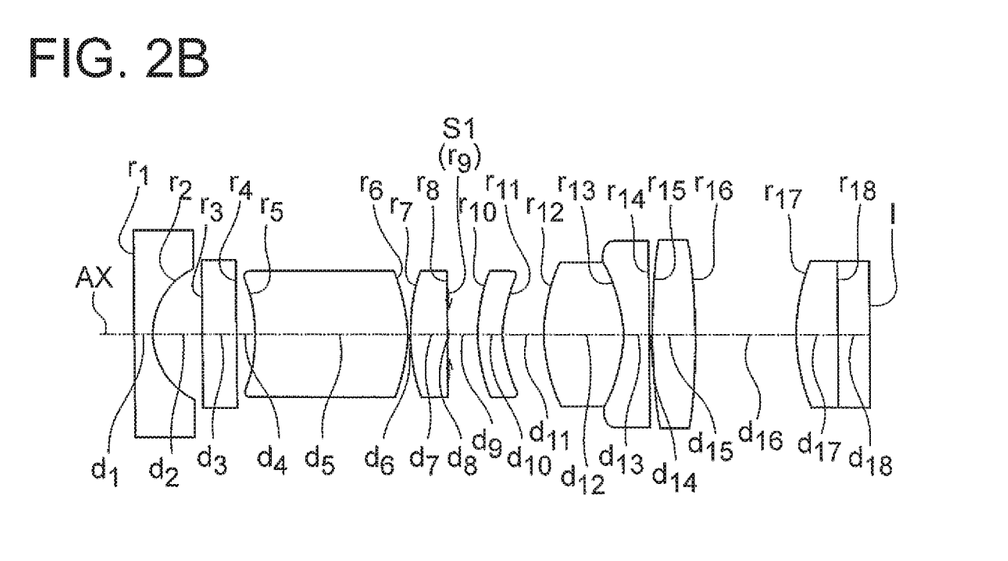
Figures 3A, 3B, 3C:
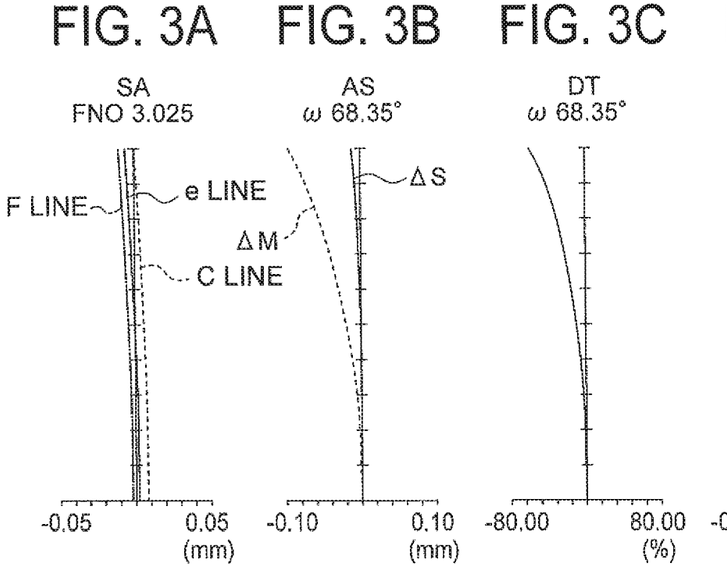
FIG. 3A, FIG. 3B, FIG. 3C, FIG. 3D, FIG. 3E, FIG. 3F, FIG. 3G, and FIG. 3H are aberration diagrams of the objective optical system according to the example 1.
Figure 3D:
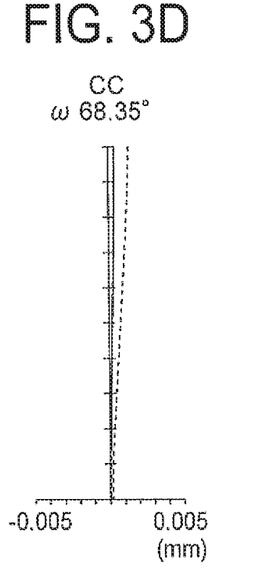
Figures 3E, 3F, 3G:
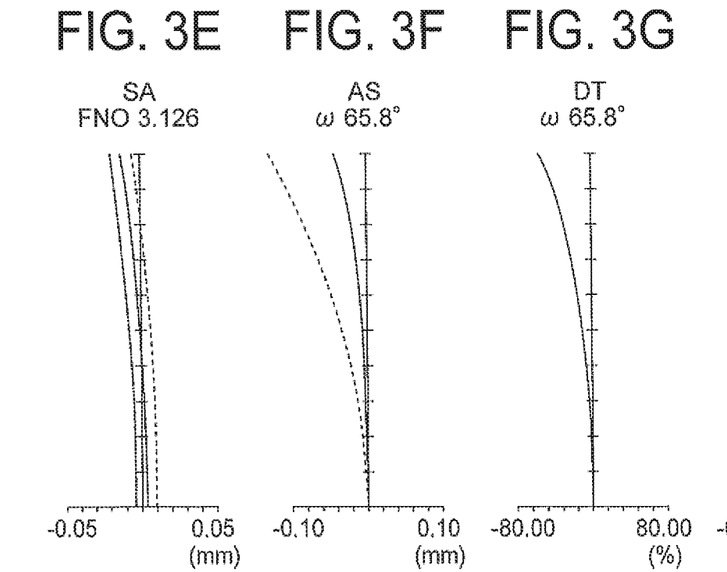
Figure 3H:
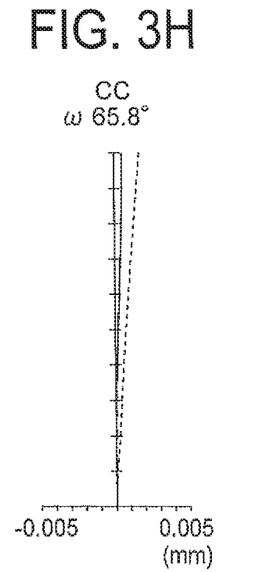

An objective optical system according to an example 1 will be described below. FIG. 2A is a cross-sectional view in a normal observation state (an object point at a long distance) of the objective optical system according to the present example, and FIG. 2B is a cross-sectional view in a close observation state (an object point at a short distance) of the objective optical system according to the present example.

The objective optical system according to the present example includes in order from an object side, a first group G1 having a positive refractive power, an aperture stop S1, a second group G2 having a negative refractive power, and a third group G3 having a positive refractive power.

The first group G1 having a positive refractive power includes in order from the object side, a first negative lens L1 which is a planoconcave lens having a concave surface directed toward an image side, a plane parallel plate F1, a second positive meniscus lens L2 having a convex surface directed toward the image side, and a third positive lens L3 which is a planoconvex lens having a convex surface directed toward the object side. The aperture stop S1 is disposed on a rear side (the image pickup surface I side) of the first group G1.

The second group G2 having a negative refractive power includes a fourth negative meniscus lens L4 having a convex surface directed toward the object side. The fourth negative meniscus lens L4, at the time of focusing from the normal observation state (FIG. 2A) to the close observation state (FIG. 2B), moves toward the image side (the image pickup surface I side) along an optical axis AX.

The third group G3 having a positive refractive power includes in order from the object side, a fifth positive lens L5 which is a biconvex lens, a sixth negative lens L6 which is a biconcave lens, a seventh positive lens L7 which is a biconvex lens, and an eighth positive lens L8 which is a planoconvex lens having a convex surface directed toward the object side.

The fifth positive lens L5 and the sixth negative lens L6 are cemented and form a cemented lens CL1.

An image sensor which is not shown in the diagram is disposed at a rear side (the image pickup surface I side) of the third group G3. A cover glass CG is affixed to a front surface (object-side surface) of the image sensor. In the present example, the eighth positive lens L8 is cemented to a front surface (object-side surface) of the cover glass CG. The eighth positive lens L8 has a function of a field lens.

The plane parallel plate F1 is a filter having a coating for cutting specific wavelengths such as 1060 nm of YAG (yttrium aluminum garnet) laser, 810 nm of semiconductor laser, or an infrared region, applied thereon.

FIG. 3A, FIG. 3B, FIG. 3C, and FIG. 3D show a spherical aberration (SA), an astigmatism (AS), distortion (DT), and a chromatic aberration of magnification (CC) in the normal observation state of the present example. FIG. 3E, FIG. 3F, FIG. 3G, and FIG. 3H show a spherical aberration (SA), an astigmatism (AS), distortion (DT), and a chromatic aberration of magnification (CC) in the close observation state of the present example.

The aberration diagrams show aberration for wavelengths 656.3 nm (C-line), 486.1 nm (F-line), and 546.1 nm (e-line). Moreover, in each aberration diagram, 'ω' denotes a half angle of view. Similar reference numerals are used for aberration diagrams described below.

Example 2

Figure 4A:
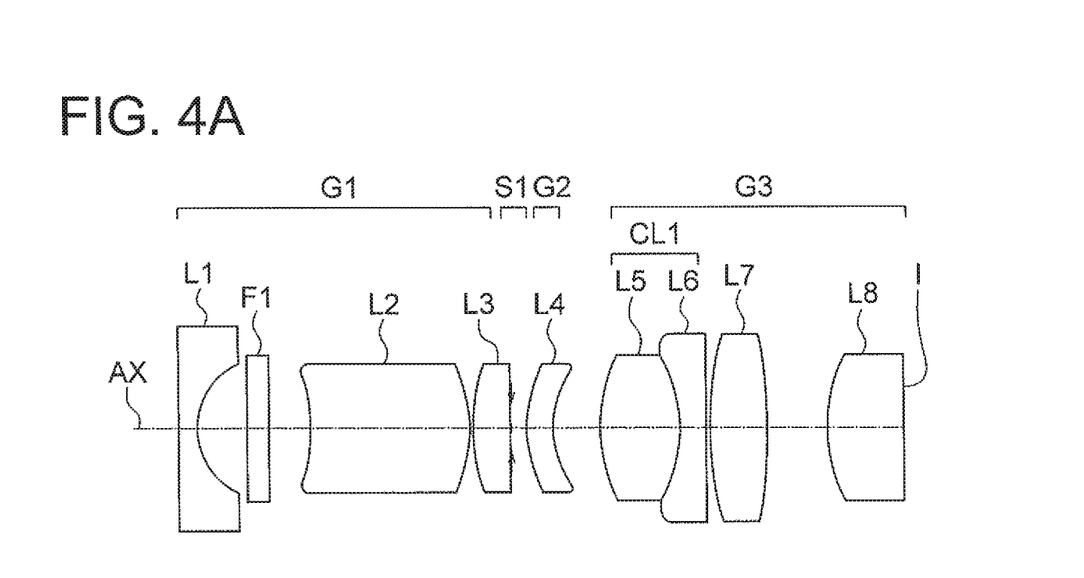
FIG. 4A and FIG. 4B are lens cross-sectional views of an objective optical system according to an example 2.
Figure 4B:
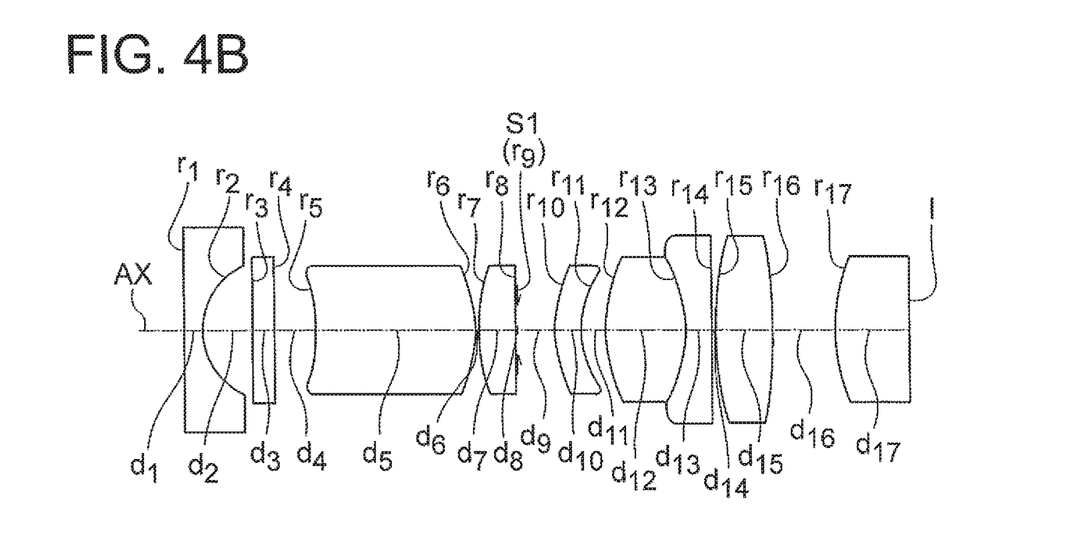
Figure 5A:
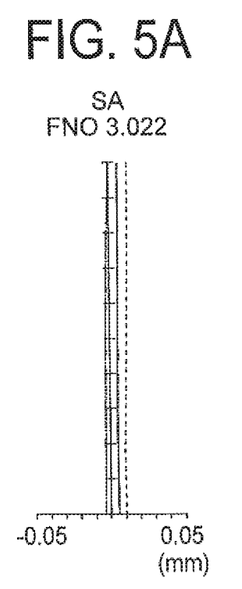
FIG. 5A, FIG. 5B, FIG. 5C, FIG. 5D, FIG. 5E, FIG. 5F, FIG. 5G, and FIG. 5H are aberration diagrams of the objective optical system according to the example 2.
Figure 5B:
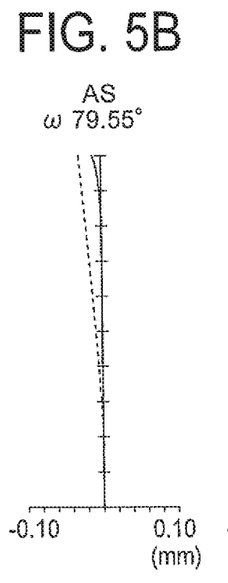
Figure 5C:
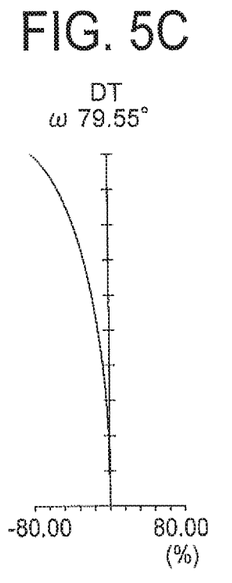
Figure 5D:
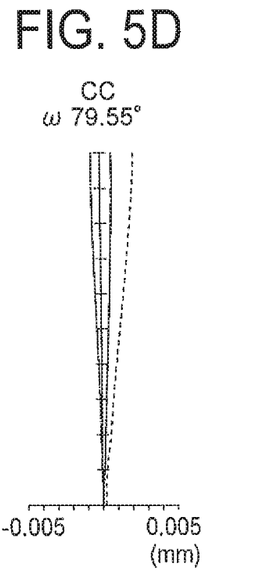
Figure 5E:
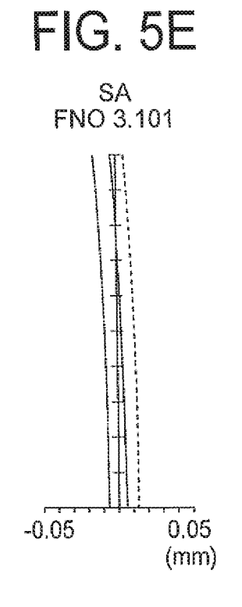
Figure 5F:
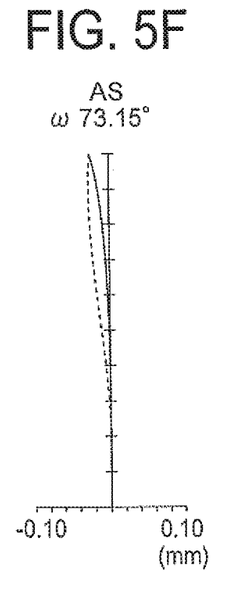
Figure 5G:
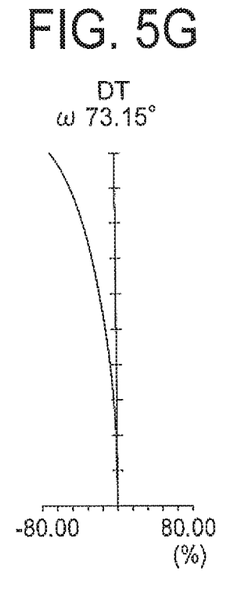
Figure 5H:
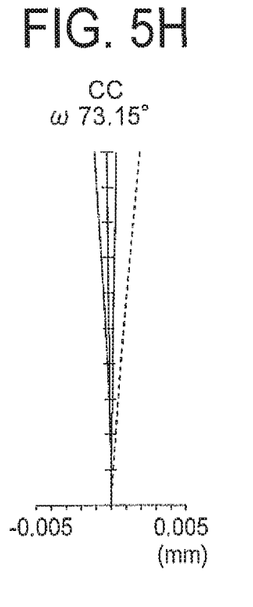

An objective optical system according to an example 2 will be described below. FIG. 4A is a cross-sectional view in a normal observation state (an object point at a long distance) of the objective optical system according to the present example, and FIG. 4B is a cross-sectional view in a close observation state (an object point at a short distance) of the objective optical system according to the present example.

The objective optical system according to the present example includes in order from an object side, a first group G1 having a positive refractive power, an aperture stop S1, a second group G2 having a negative refractive power, and a third group G3 having a positive refractive power.

The first group G1 having a positive refractive power includes in order from the object side, a first negative lens L1 which is a planoconcave lens having a concave surface directed toward an image side, a plane parallel plate F1, a second positive meniscus lens L2 having a convex surface directed toward the image side, and a third positive lens L3 which is a planoconvex lens having a convex surface directed toward the object side. The aperture stop S1 is disposed on a rear side (the image pickup surface I side) of the first group G1.

The second group G2 having a negative refractive power includes a fourth negative meniscus lens L4 having a convex surface directed toward the object side. The fourth negative meniscus lens L4, at the time of focusing from the normal observation state (FIG. 4A) to the close observation state (FIG. 4B), moves toward the image side (the image pickup surface I side) along an optical axis AX.

The third group G3 having a positive refractive power includes in order from the object side, a fifth positive lens L5 which is a biconvex lens, a sixth negative lens L6 which is a biconcave lens, a seventh positive lens L7 which is a biconvex lens, and an eighth positive lens L8 which is a planoconvex lens having a convex surface directed toward the object side. The fifth positive lens L5 and the sixth negative lens L6 are cemented and form a cemented lens CL1.

An image sensor which is not shown in the diagram is disposed at a rear side (the image pickup surface I side) of the third group G3. The eighth positive lens L8 is affixed to a front surface (object-side surface) of the image sensor. In the present example, the eighth positive lens L8 functions also as a cover glass. Moreover, the eighth positive lens L8 has a function of a field lens.

The plane parallel plate F1 is a filter having a coating for cutting specific wavelengths such as 1060 nm of YAG laser, 810 nm of semiconductor laser, or an infrared region, applied thereon.

FIG. 5A, FIG. 5B, FIG. 5C, and FIG. 5D show a spherical aberration (SA), an astigmatism (AS), a distortion (DT), and a chromatic aberration of magnification (CC) in the normal observation state of the present example. FIG. 5E, FIG. 5F, FIG. 5G, and FIG. 5H show a spherical aberration (SA), an astigmatism (AS), a distortion (DT), and a chromatic aberration of magnification (CC) in the close observation state of the present example.

Example 3

Figure 6A:
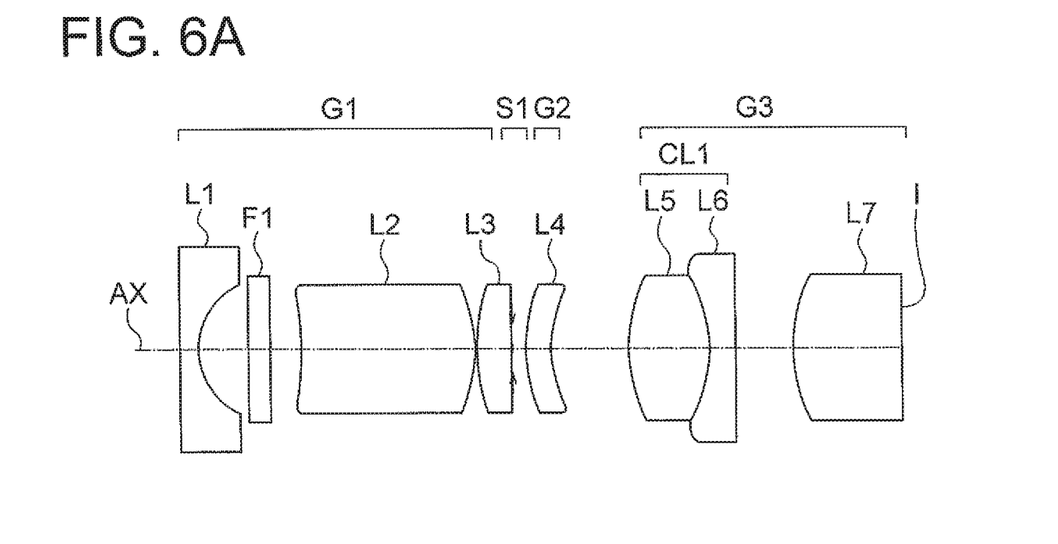
FIG. 6A and FIG. 6B are lens cross-sectional views of an objective optical system according to an example 3.
Figure 6B:
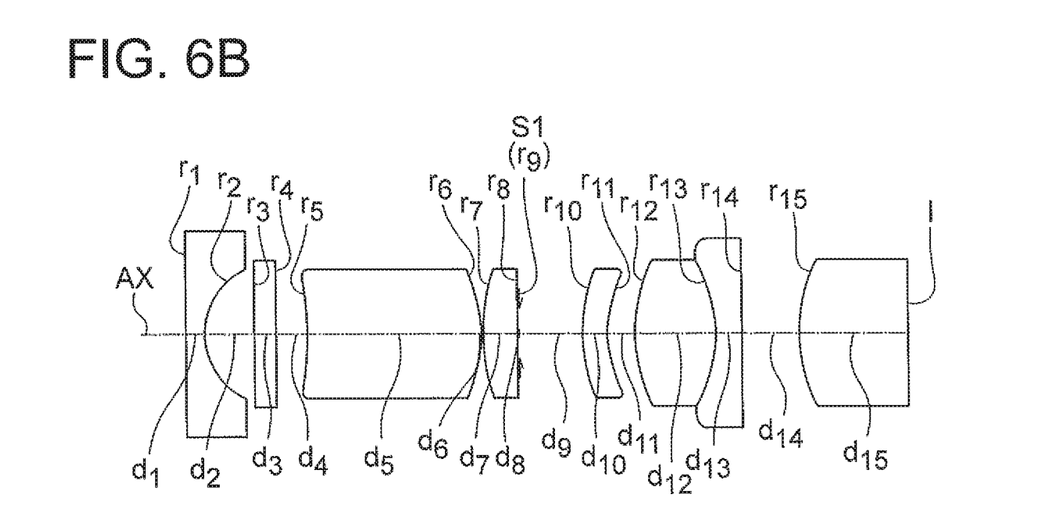
Figure 7A:
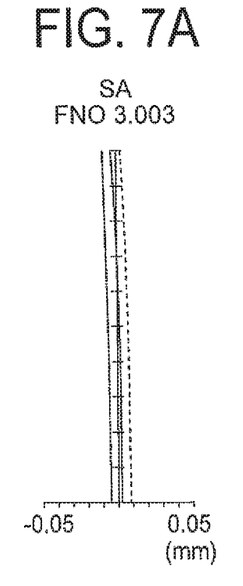
FIG. 7A, FIG. 7B, FIG. 7C, FIG. 7D, FIG. 7E, FIG. 7F, FIG. 7G, and FIG. 7H are aberration diagrams of the objective optical system according to the example 3.
Figure 7B:
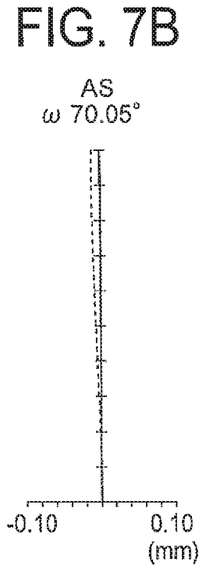
Figure 7C:
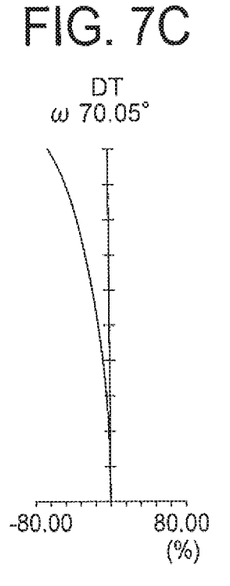
Figure 7D:
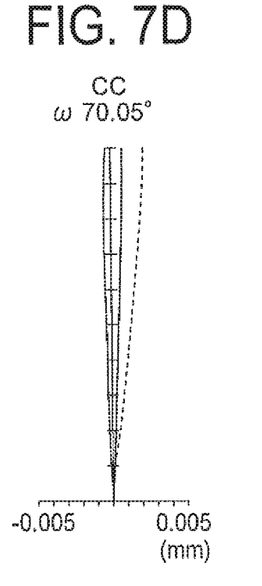
Figure 7E:
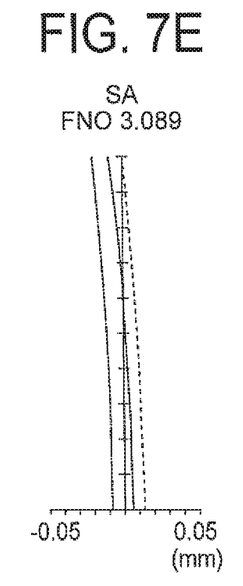
Figure 7F:
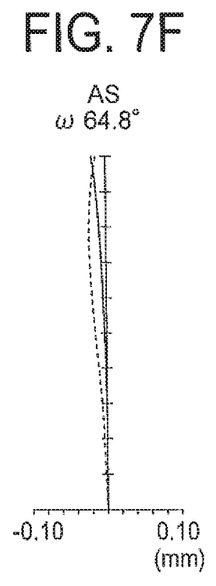
Figure 7G:
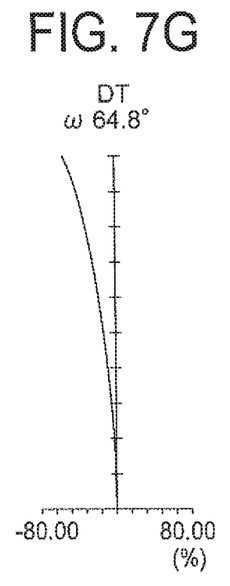
Figure 7H:
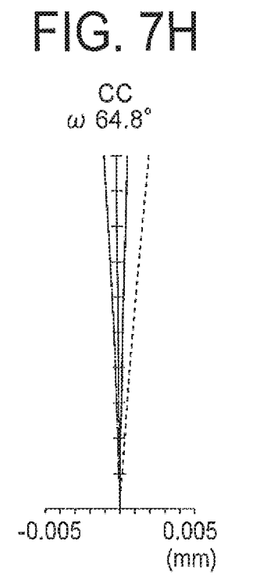

An objective optical system according to an example 3 will be described below. FIG. 6A is a cross-sectional view in a normal observation state (an object point at a long distance) of the objective optical system according to the present example, and FIG. 6B is a cross-sectional view in a close observation state (an object point at a short distance) of the objective optical system according to the present example.

The objective optical system according to the present example includes in order from an object side, a first group G1 having a positive refractive power, an aperture stop S1, a second group G2 having a negative refractive power, and a third group G3 having a positive refractive power.

The first group G1 having a positive refractive power includes in order from the object side, a first negative lens L1 which is a planoconcave lens having a concave surface directed toward an image side, a plane parallel plate F1, a second positive meniscus lens L2 having a convex surface directed toward the image side, and a third positive meniscus lens L3 having a convex surface directed toward the object side. The aperture stop S1 is disposed on a rear side (the image pickup surface I side) of the first group G1.

The second group G2 having a negative refractive power includes a fourth negative meniscus lens L4 having a convex surface directed toward the object side. The fourth negative meniscus lens L4, at the time of focusing from the normal observation state (FIG. 6A) to the close observation state (FIG. 6B), moves toward the image side (the image pickup surface I side) along an optical axis AX.

The third group G3 having a positive refractive power includes a fifth lens L5 which is a biconvex positive lens, a sixth meniscus lens L6 which is a negative lens having a convex surface directed toward the image side, and a seventh lens L7 which is a planoconvex positive lens having a convex surface directed toward the object side. The fifth lens L5 having a positive refractive power and the sixth meniscus lens L6 having a negative refractive power are cemented and form a cemented lens CL1.

An image sensor which is not shown in the diagram is disposed at a rear side (the image pickup surface I side) of the third group G3. The seventh positive lens L7 is affixed to a front surface (object-side surface) of the image sensor. In the present example, the seventh positive lens L7 functions also as a cover glass. Moreover, the seventh positive lens L7 has a function of a field lens.

The plane parallel plate F1 is a filter having a coating for cutting specific wavelengths such as 1060 nm of YAG laser, 810 nm of semiconductor laser, or an infrared region, applied thereon.

FIG. 7A, FIG. 7B, FIG. 7C, and FIG. 7D show a spherical aberration (SA), an astigmatism (AS), a distortion (DT), and a chromatic aberration of magnification (CC) in the normal observation state of the present example. FIG. 7E, FIG. 7F, FIG. 7G, and FIG. 7H show a spherical aberration (SA), an astigmatism (AS), a distortion (DT), and a chromatic aberration of magnification (CC) in the close observation state of the present example.

Example 4

Figure 8A:
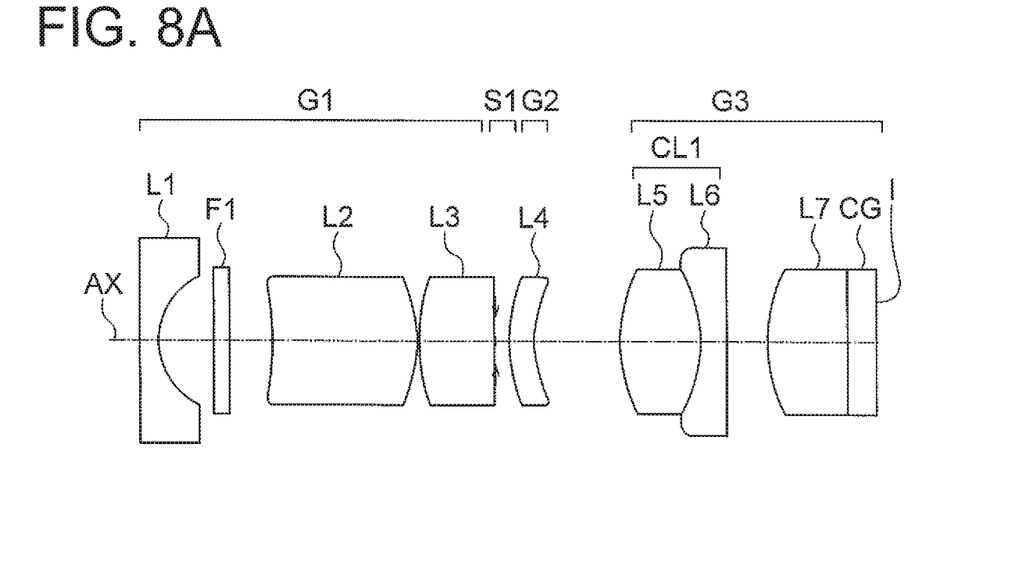
FIG. 8A and FIG. 8B are lens cross-sectional views of an objective optical system according to an example 4.
Figure 8B:
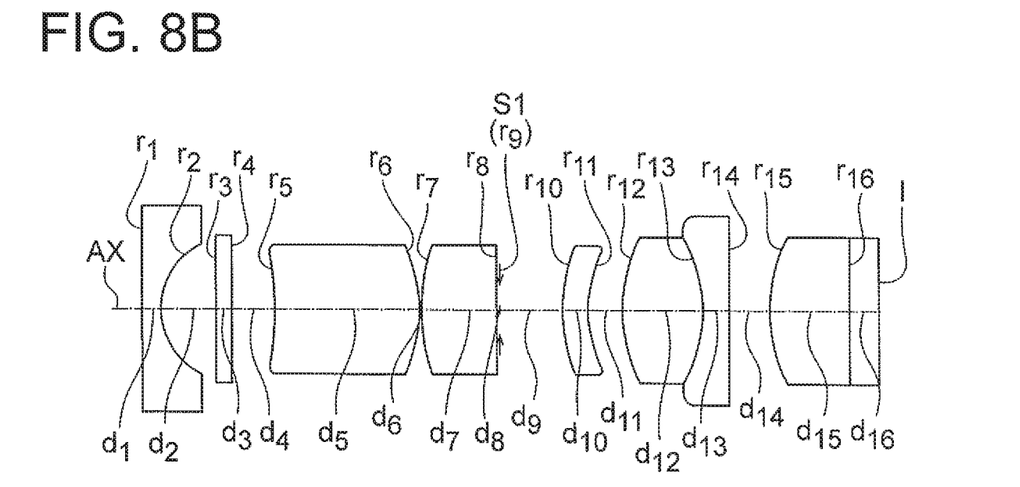
Figure 9A:
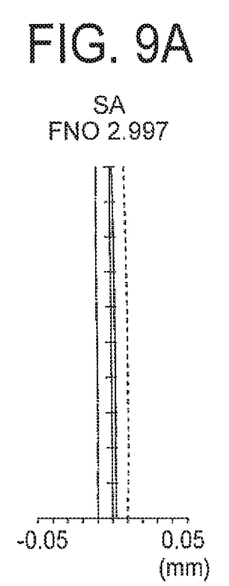
FIG. 9A, FIG. 9B, FIG. 9C, FIG. 9D, FIG. 9E, FIG. 9F, FIG. 9G, and FIG. 9H are aberration diagrams of the objective optical system according to the example 4.
Figure 9B:
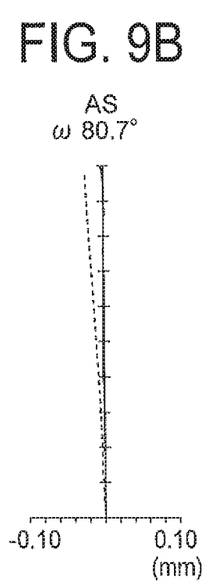
Figure 9C:
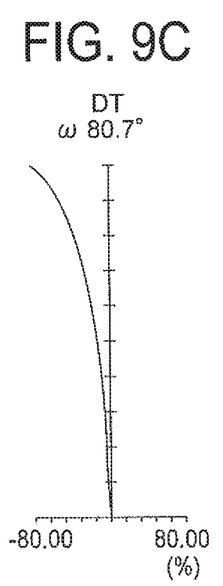
Figure 9D:
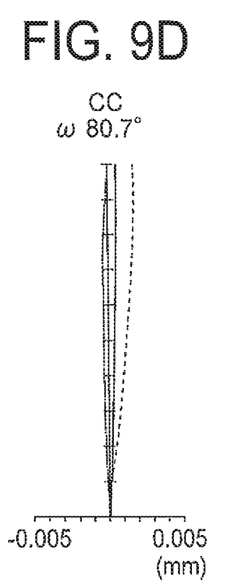
Figure 9E:
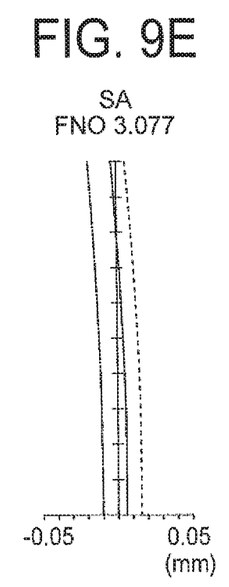
Figure 9F:
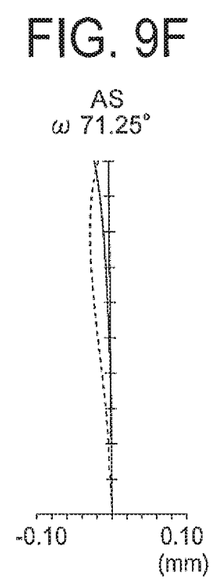
Figure 9G:
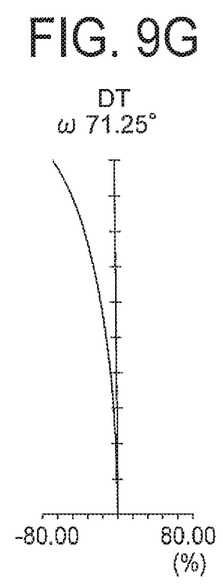
Figure 9H:
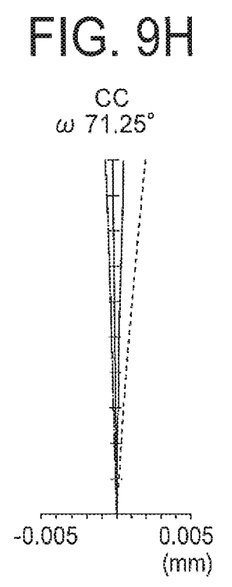

An objective optical system according to an example 4 will be described below. FIG. 8A is a cross-sectional view in a normal observation state (an object point at a long distance) of the objective optical system according to the present example, and FIG. 8B is a cross-sectional view in a close observation state (an object point at a short distance) of the objective optical system according to the present example.

The objective optical system according to the present example includes in order from an object side, a first group G1 having a positive refractive power, an aperture stop S1, a second group G2 having a negative refractive power, and a third group G3 having a positive refractive power.

The first group G1 having a positive refractive power includes in order from the object side, a first negative lens L1 which is a planoconcave lens having a concave surface directed toward an image side, a plane parallel plate F1, a second positive meniscus lens L2 having a convex surface directed toward the image side, and a third positive meniscus lens L3 having a convex surface directed toward the object side. The aperture stop S1 is disposed on a rear side (the image pickup surface I side) of the first group G1.

The second group G2 having a negative refractive power includes a fourth negative meniscus lens L4 having a convex surface directed toward the object side. The fourth negative meniscus lens L4, at the time of focusing from the normal observation state (FIG. 8A) to the close observation state (FIG. 8B), moves toward the image side (image plane I) along an optical axis AX.

The third group G3 having a positive refractive power includes a fifth positive lens L5 which is a biconvex lens, a sixth negative lens L6 which is a biconcave lens, and a seventh positive lens L7 which is a planoconvex lens having a convex surface directed toward the object side. The fifth positive lens L5 and the sixth negative lens L6 are cemented and form a cemented lens CL1.

An image sensor which is not shown in the diagram is disposed at a rear side (the image pickup surface I side) of the third group G3. A cover glass CG is affixed to a front surface (object-side surface) of the image sensor. In the present example, the seventh positive lens L7 is cemented to a front surface of the cover glass CG. The seventh positive lens L7 has a function of a field lens.

The plane parallel plate F1 is a filter having a coating for cutting specific wavelengths such as 1060 nm of YAG laser, 810 nm of semiconductor laser, or an infrared region, applied thereon.

FIG. 9A, FIG. 9B, FIG. 9C, and FIG. 9D show a spherical aberration (SA), an astigmatism (AS), a distortion (DT), and a chromatic aberration of magnification (CC) in the normal observation state of the present example. FIG. 9E, FIG. 9F, FIG. 9G, and FIG. 9H show a spherical aberration (SA), an astigmatism (AS), a distortion (DT), and a chromatic aberration of magnification (CC) in the close observation state of the present example.

Numerical data for each example is shown below. Regarding symbols, r denotes a radius of curvature of each lens surface, d denotes a distance between two lenses, ne denotes a refractive index of each lens for an e-line, vd denotes Abbe's number for each lens, Fno denotes an F-number, ω denotes the half angle of view, and IH denotes an image height.

Example 1

Unit mm

Surface data

| Surface no. | r | d | ne | vd |
|---|---|---|---|---|
| 1 | ∞ | 0.324 | 1.88815 | 40.76 |
| 2 | 1.2000 | 0.800 | | |
| 3 | ∞ | 0.572 | 1.52300 | 65.13 |
| 4 | ∞ | 0.274 | | |
| 5 | −2.8616 | 2.586 | 1.48915 | 70.23 |
| 6 | −2.4484 | 0.044 | | |
| 7 | 3.5294 | 0.620 | 1.65222 | 33.79 |
| 8 | ∞ | 0.030 | | |
| 9(Stop) | ∞ | Variable | | |
| 10 | 3.1936 | 0.428 | 1.58482 | 40.75 |
| 11 | 2.0120 | Variable | | |
| 12 | 3.4274 | 1.314 | 1.73234 | 54.68 |
| 13 | −2.6080 | 0.428 | 1.93429 | 18.90 |
| 14 | 115.3248 | 0.058 | | |
| 15 | 9.4518 | 0.732 | 1.48915 | 70.23 |
| 16 | −9.4518 | 1.662 | | |
| 17 | 3.1732 | 0.720 | 1.51825 | 64.14 |
| 18 | ∞ | 0.500 | 1.50700 | 65.00 |
| 19(Image pickup surface) | | | | |

Variable data

| | Normal observation state | Close observation state |
|---|---|---|
| focal length | 1.049 | 1.060 |
| Fno | 3.03 | 3.13 |
| Object distance | 24.0 | 7.9 |
| d9 | 0.228 | 0.470 |
| d11 | 1.144 | 0.702 |
| ω | 68.35° | 65.8° |
| IH = 1.0 mm | | |

Example 2

Unit mm

Surface data

| Surface no. | r | d | ne | vd |
|---|---|---|---|---|
| 1 | ∞ | 0.383 | 1.88815 | 40.76 |
| 2 | 1.3402 | 0.838 | | |
| 3 | ∞ | 0.450 | 1.52300 | 65.13 |
| 4 | ∞ | 0.752 | | |
| 5 | −3.4350 | 2.932 | 1.48915 | 70.23 |
| 6 | −2.8851 | 0.050 | | |
| 7 | 3.9404 | 0.690 | 1.65222 | 33.79 |
| 8 | ∞ | 0.032 | | |
| 9(Stop) | ∞ | Variable | | |
| 10 | 2.7683 | 0.478 | 1.58482 | 40.75 |
| 11 | 1.9215 | Variable | | |
| 12 | 3.2875 | 1.467 | 1.73234 | 54.68 |
| 13 | −2.9087 | 0.479 | 1.93429 | 18.90 |
| 14 | 15.6199 | 0.064 | | |
| 15 | 6.3609 | 1.066 | 1.48915 | 70.23 |

-continued

| Unit mm | | | | |
|---|---|---|---|---|
| 16 | −10.4249 | 1.089 | | |
| 17 | 3.2323 | 1.372 | 1.51825 | 64.14 |
| 18(Image pickup surface) | | | | |

| Variable data | | |
|---|---|---|
| | Normal observatioin state | Close observation state |
| focal length | 0.995 | 1.014 |
| Fno | 3.02 | 3.10 |
| Object distance | 20.0 | 8.75 |
| d9 | 0.271 | 0.655 |
| d11 | 0.856 | 0.472 |
| ω | 79.55° | 73.15° |
| IH = 1.0 mm | | |

Example 3

| Unit mm | | | | |
|---|---|---|---|---|
| Surface data | | | | |
| Surface no. | r | d | ne | vd |
| 1 | ∞ | 0.400 | 1.88815 | 40.76 |
| 2 | 1.4005 | 0.950 | | |
| 3 | ∞ | 0.400 | 1.52300 | 65.13 |
| 4 | ∞ | 0.607 | | |
| 5 | −6.2988 | 3.394 | 1.48915 | 70.23 |
| 6 | −2.7963 | 0.052 | | |
| 7 | 4.5157 | 0.650 | 1.65222 | 33.79 |
| 8 | 16.4773 | 0.030 | | |
| 9(Stop) | ∞ | Variable | | |
| 10 | 3.1858 | 0.500 | 1.58482 | 40.75 |
| 11 | 2.4423 | Variable | | |
| 12 | 3.2042 | 1.533 | 1.73234 | 54.68 |
| 13 | −2.6830 | 0.500 | 1.93429 | 18.90 |
| 14 | −262.1562 | 1.164 | | |
| 15 | 3.1241 | 2.100 | 1.51825 | 64.14 |
| 16(Image pickup surface) | | | | |

| Variable data | | |
|---|---|---|
| | Normal observation state | Close observation state |
| focal length | 1.064 | 1.090 |
| Fno | 3.00 | 3.09 |
| Object distance | 27.5 | 9.20 |
| d9 | 0.287 | 1.277 |
| d11 | 1.534 | 0.544 |
| ω | 70.05° | 64.8° |
| IH = 1.0 mm | | |

Example 4

| Unit mm | | | | |
|---|---|---|---|---|
| Surface data | | | | |
| Surface no. | r | d | ne | vd |
| 1 | ∞ | 0.383 | 1.88815 | 40.76 |
| 2 | 1.3402 | 0.992 | | |
| 3 | ∞ | 0.300 | 1.52300 | 65.13 |
| 4 | ∞ | 0.741 | | |
| 5 | −4.1863 | 2.645 | 1.48915 | 70.23 |

-continued

| Unit mm | | | | |
|---|---|---|---|---|
| 6 | −2.6082 | 0.050 | | |
| 7 | 5.1937 | 1.365 | 1.88815 | 40.76 |
| 8 | 23.0350 | 0.060 | | |
| 9(Stop) | ∞ | Variable | | |
| 10 | 2.8250 | 0.480 | 1.58482 | 40.75 |
| 11 | 2.1802 | Variable | | |
| 12 | 2.8773 | 1.467 | 1.73234 | 54.68 |
| 13 | −2.6261 | 0.479 | 1.93429 | 18.90 |
| 14 | 70.2133 | 0.770 | | |
| 15 | 2.9523 | 1.460 | 1.51825 | 64.14 |
| 16 | ∞ | 0.550 | 1.50700 | 63.26 |
| 17(Image pickup surface) | | | | |

| Variable data | | |
|---|---|---|
| | Normal observation state | Close observation state |
| focal length | 1.024 | 1.046 |
| Fno | 3.00 | 3.08 |
| Object distance | 25.5 | 8.78 |
| d9 | 0.243 | 1.202 |
| d11 | 1.544 | 0.585 |
| ω | 80.7° | 71.25° |
| IH = 1.0 mm | | |

Corresponding values of the conditional expressions are shown below.

| Conditional expression | | | | |
|---|---|---|---|---|
| | Example1 | Example2 | Example3 | Example4 |
| (1) ff/f | 5.84 | 6.27 | 5.67 | 5.57 |
| (2) fg2/f | −10.24 | −13.64 | −22.38 | −22.00 |
| (3) rf/f | 3.03 | 3.25 | 2.94 | 2.88 |
| (4) df/ff | 0.20 | 0.22 | 0.35 | 0.35 |
| (5) dn/f | 0.23 | 0.38 | 0.94 | 0.94 |
| (6) fg2/fg1 | −4.68 | −5.72 | −7.62 | −7.72 |
| (7) fg2/fg3 | −2.96 | −3.72 | −6.27 | −6.50 |
| (8) r2/f | 1.14 | 1.35 | 1.32 | 1.31 |
| (9) f1/ff | −0.22 | −0.24 | −0.26 | −0.26 |
| (10) df/dn | 5.04 | 3.57 | 2.12 | 2.10 |

Various embodiments of the present invention have been described heretofore. However, the present invention is not restricted to the embodiments described above, and embodiments in which arrangement of the abovementioned embodiments are combined appropriately without departing from the scope of the invention are also in the category of the present invention.

(Appended Modes)

An invention having the following arrangement is derived from the examples described above.

(Appended Mode 1)

An objective optical system, comprising in order from an object side:

a first group having a positive refractive power;

a second group having a negative refractive power; and a third group having a positive refractive power, wherein focusing is carried out by moving the second group, and a lens nearest to image is a planoconvex positive lens having a convex surface directed toward the object side, and a flat surface of the planoconvex positive lens is one of a surface which is affixed directly to an image pickup surface and a surface which is cemented to a cover glass formed on the image pickup surface, and the objective optical system satisfies the following conditional expression (1)

$$5 < ff/f < 8 \tag{1}$$

where, ff denotes a focal length of the planoconvex positive lens disposed nearest to image, and f denotes a focal length of the overall objective optical system at the time of normal observation.

(Appended Mode 2)

The objective optical system according to appended mode (2), wherein the objective optical system satisfies the following conditional expression (2)

$$-24 < fg2/f < -8 \tag{2}$$

where, fg2 denotes a focal length of the second group, and f denotes the focal length of the overall objective optical system at the time of normal observation.

(Appended Mode 3)

The objective optical system according to one of appended modes 1 and 2, wherein the objective optical system satisfies any of the following conditional expressions (3), (4), (5), (6), (7), (8), (9), and (10)

$$2 < rf/f < 4 \tag{3}$$

$$0.15 < df/ff < 0.4 \tag{4}$$

$$0.2 < dn/f < 1.2 \tag{5}$$

$$-8 < fg2/fg1 < -4 \tag{6}$$

$$-7.6 < fg2/fg3 < -2.4 \tag{7}$$

$$1.05 < r2/f < 1.45 \tag{8}$$

$$-0.34 < f1/ff < -0.18 \tag{9}$$

$$1.2 < df/dn < 5.6 \tag{10}$$

where, ff denotes a focal length of the planoconvex positive lens disposed nearest to image, f denotes a focal length of the overall objective optical system at the time of normal observation, rf denotes a radius of curvature of an object-side surface of the positive lens disposed nearest to image, df denotes a distance from an object-side surface of the positive lens disposed nearest to image up to the image pickup surface, dn denotes an amount of movement of the second group, fg1 denotes a focal length of the first group, fg2 denotes the focal length of the second group, fg3 denotes a focal length of the third group, r2 denotes a radius of curvature of an image-side surface of the first lens disposed nearest to object, and f1 denotes a focal length of the first lens disposed nearest to object.

(Appended Mode 4)

An objective optical system, comprising in order from an object side;

a first group;

a second group; and a third group, wherein focusing is carried out by moving the second group, and a lens nearest to image is a planoconvex positive lens having a convex surface directed toward the object side, and a flat surface of the planoconvex positive lens is one of a surface which is affixed directly to an image pickup surface and a surface which is cemented to a cover glass formed on the image pickup surface, and the objective optical system satisfies the following conditional expression (1')

$$5.5 < ff/f < 6 \tag{1'}$$

where, ff denotes a focal length of the planoconvex positive lens disposed nearest to image, and f denotes a focal length of the overall objective optical system at the time of normal observation.

The present invention is useful for an objective optical system which has a focusing function, and particularly, to an objective optical system for endoscope which enables a close observation, and other objective optical systems which are suitable for photography by a small-size camera for household use.

The present invention shows an effect that it is possible to provide a bright objective optical system with a high performance, suitable for a small-size image sensor with a large number of pixels, in which the focusing in accordance with a change in the focal length is possible, and the manufacturing-error sensitivity is lowered.

What is claimed is:

1. An objective optical system, consists of in order from an object side:

a first group having a positive refractive power;

a second group having a negative refractive power; and a third group having a positive refractive power, wherein focusing is carried out by moving the second group, and a lens nearest to image is a planoconvex positive lens having a convex surface directed toward the object side, and a flat surface of the planoconvex positive lens is one of a surface which is affixed directly to an image pickup surface and a surface which is cemented to a cover glass formed on the image pickup surface, and the objective optical system satisfies the following conditional expression (1)

$$5 < ff/f < 8 \tag{1}$$

where, ff denotes a focal length of the planoconvex positive lens disposed nearest to image, and f denotes a focal length of the overall objective optical system at the time of normal observation.

2. The objective optical system according to claim 1, wherein the objective optical system satisfies the following conditional expression (2)

$$-24 < fg2/f < -8 \tag{2}$$

where, fg2 denotes a focal length of the second group, and f denotes the focal length of the overall objective optical system at the time of normal observation.

* * * * *